United States Patent
Hudson et al.

(10) Patent No.: US 6,336,457 B1
(45) Date of Patent: Jan. 8, 2002

(54) BODY CAVITY TUBE SECURING DEVICE AND METHOD OF USING SAME

(75) Inventors: Michael S. Hudson, San Diego, CA (US); Matthew P. Smith, 4639 Larkspur St., San Diego, CA (US) 92107; Douglas A. Moriarty, P.O. Box 81451, San Diego, CA (US) 92138

(73) Assignees: Douglas A. Moriarty; Matthew P. Smith, both of San Diego, CA (US)

( * ) Notice: Subject to any disclaimer, the term of this patent is extended or adjusted under 35 U.S.C. 154(b) by 0 days.

(21) Appl. No.: 09/454,165

(22) Filed: Nov. 17, 1999

(51) Int. Cl.[7] .............................................. A61M 16/00
(52) U.S. Cl. ........................ 128/207.17; 128/DIG. 26
(58) Field of Search ..................... 128/207.17, DIG. 26

(56) References Cited

U.S. PATENT DOCUMENTS

| | | | | |
|---|---|---|---|---|
| 2,449,882 A | * | 9/1948 | Daniels ................ | 128/DIG. 26 |
| 2,727,512 A | * | 12/1955 | Muller ................. | 128/DIG. 26 |
| 2,727,513 A | * | 12/1955 | Muller ................. | 128/DIG. 26 |
| 3,648,703 A | * | 3/1972 | Manker ................ | 128/DIG. 26 |
| 4,738,662 A | * | 4/1988 | Kalt et al. ............ | 128/DIG. 26 |
| 5,042,477 A | * | 8/1991 | Lewis .................... | 128/207.17 |
| 5,188,101 A | * | 2/1993 | Tumolo ................ | 128/207.17 |
| 5,205,832 A | * | 4/1993 | Tuman ................. | 128/DIG. 26 |
| 5,282,463 A | * | 2/1994 | Hammersley .......... | 128/207.17 |
| 5,341,802 A | * | 8/1994 | Calebaugh ............. | 128/207.17 |
| 5,437,273 A | * | 8/1995 | Bates et al. ............ | 128/207.17 |

FOREIGN PATENT DOCUMENTS

| FR | 1405075 | * | 5/1965 | .......... 128/DIG. 26 |
|---|---|---|---|---|

* cited by examiner

Primary Examiner—Aaron J. Lewis
(74) Attorney, Agent, or Firm—Foley & Lardner; Bernard L. Kleinke

(57) ABSTRACT

Tube securing devices and method of using them are disclosed for immobilizing an endotracheal tube or the like in a body cavity such as in an intubated position. The device includes an elongated tube grasping arrangement having a ribbon securing device for helping to maintain the position of the tube grasping device in place. The tube grasping device includes a gripping portion disposed between its opposite ends to help limit sliding movement relative to the tube grasping assembly.

3 Claims, 2 Drawing Sheets

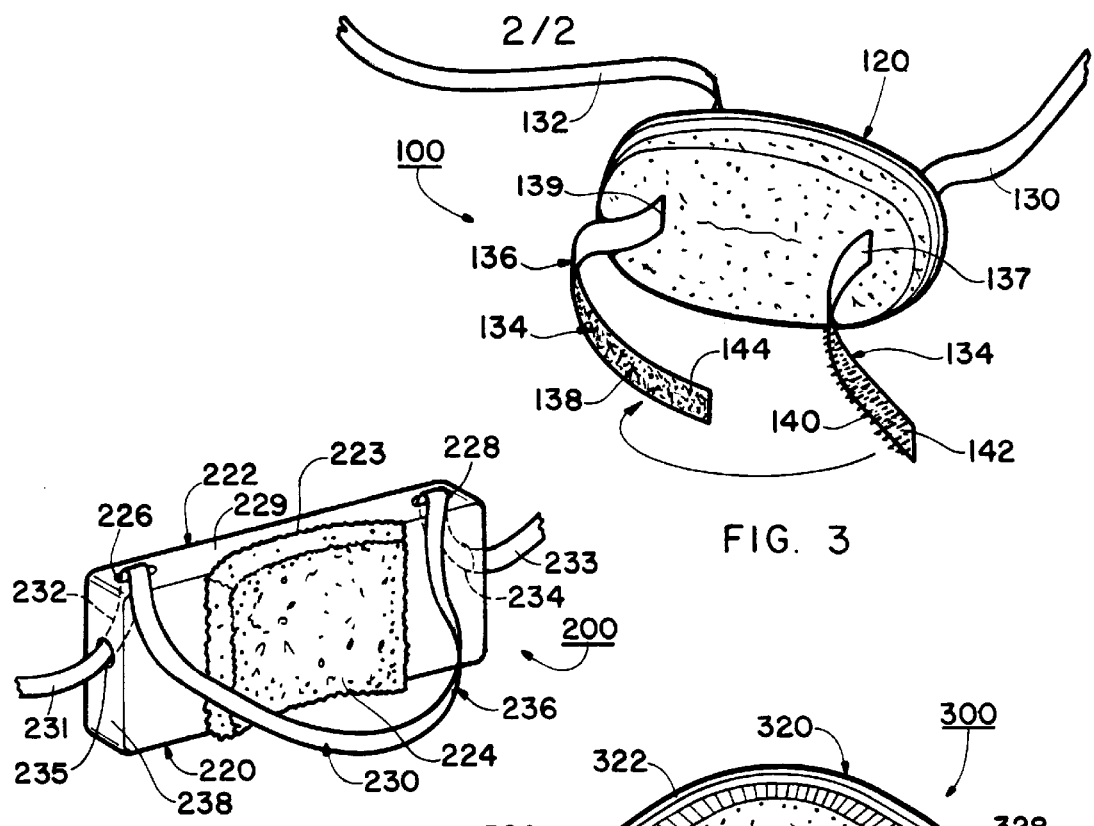
FIG. 3
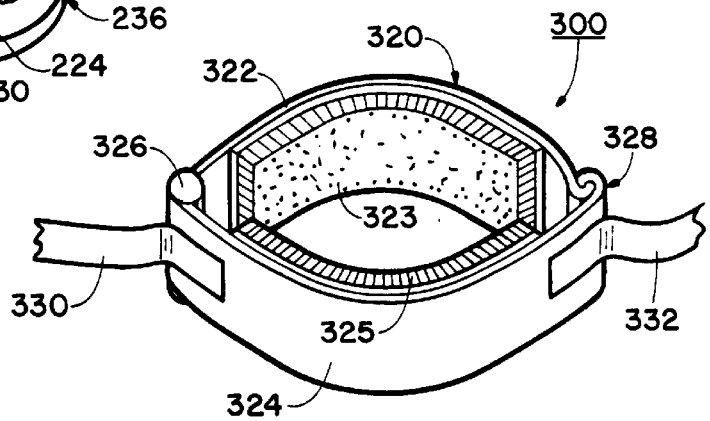
FIG. 4
FIG. 5
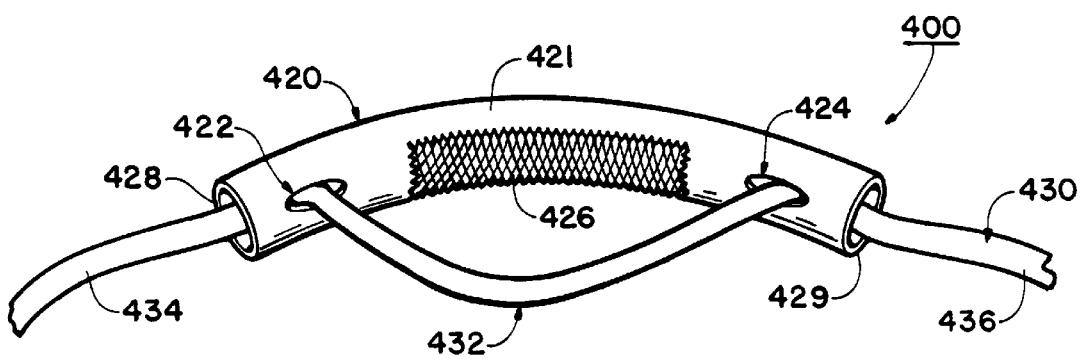
FIG. 6

BODY CAVITY TUBE SECURING DEVICE AND METHOD OF USING SAME

CROSS-REFERENCE TO RELATED APPLICATIONS

Not Applicable.

STATEMENT REGARDING FEDERALLY SPONSORED RESEARCH OR DEVELOPMENT

Not Applicable.

REFERENCE TO A "MICROFICHE APPENDIX"

Not Applicable.

BACKGROUND OF THE INVENTION

1. Technical Field

The present invention relates in general to a new and improved tube securing device and a method of using it for immobilizing a body cavity tube such as an endotracheal tube or the like in a body cavity. The invention more particularly relates to a body cavity tube securing device for limiting the movement of a body cavity tube extending from a body cavity, wherein the tube is able to be secured quickly and easily in accordance with a method of the present invention.

2. Background Art

There have been many types of tube holding devices for stabilizing a body cavity tube, such as an endotracheal tube in an intubated position. For example, reference may be made to the following U.S. patents: U.S. Pat. Nos. 3,713,448; 3,927,676; 4,437,463; 4,548,200; 4,622,034; 5,042,477; 4,844,061; 5,411,484; 5,546,938; and 5,306,233.

In the U.S. Pat. No. 4,437,463, there is disclosed a securing device for a tube which is insertable into a body cavity. The device is in the form of an elastomeric tubing which is formed into a noose for surrounding and securing the body cavity tube.

However, the patented securing device may, in certain circumstances, fail to grip securely the body cavity tube. In this regard, when emergency procedures are necessary to assist a trauma victim, there can be liquids, such as bodily fluids including blood, as well as liquids such as rain and snow when the procedure is performed out of doors, which can cause the elastomeric tubing to slip relative to the plastic body cavity tube. If the body cavity tube does not remain securely in place, it can become dislodged or at least repositioned inadvertently. Such a situation is not desirable, especially where the trauma patient is being transported.

The U.S. Pat. No. 5,042,477 discloses a medical tube holder, which helps secure an endotracheal tube inserted within a body cavity of a patient. The tube holder includes an elongated elastomeric tube having a slit disposed intermediate its ends. A securing strap is threaded through the tubing and a middle portion of the strap extends through the slit to form a loop for receiving the medical tube. The securing strap is then wrapped about the body of the patient and tied in place at its ends.

Such an arrangement is also subject to slippage and loosening of the holder relative to the body cavity tube. In this regard, the loop of strap entirely surrounds the endotracheal tube and can slip relative thereto, especially when bodily fluids and other fluids come into contact therewith. Additionally, the elastomeric tube which receives the strap is pulled into tight engagement with the face of the patient. Such an arrangement is less than comfortable for the patient.

Therefore, it is important for such a securing device to retain the body cavity tube in a fixed immobile position relative to the body of the patient, while the person is being transported. The body cavity tube must be retained in place, even where fluids are present and can make the securing device and the body cavity tube slippery and thus more difficult to secure in a fast and convenient manner. Also, the securing device should be able to fix the body cavity tube in position in a relatively comfortable manner, without adding discomfort or trauma to the patient.

Additionally, it is very important to be able to secure the body cavity tube in place in a rapid and efficient manner, especially where emergency conditions prevail. In the U.S. Pat. No. 4,622,034, there is disclosed a medical tube holder, which includes an apertured foam strip, which wraps about the head of the user, and the body cavity tube may be inserted into a pair of aligned holes in the strip and then into the body orifice. Such an arrangement would be very difficult to manipulate in a rapid and efficient manner, in that the holes must be properly aligned and held in place exactly in alignment with the body cavity opening, such as the mouth of the patient. Once the alignment is somehow achieved, then the body cavity tube is inserted through the aligned apertures in the strip. Such a manipulation is awkward and difficult by a single person in a rapid and efficient manner, and require an intolerable length of time in severe weather conditions.

Therefore, it would be highly desirable to have a new and improved device and method for immobilizing a body cavity tube in place in a very secure manner, and yet be able to accomplish the attachment to the tube in a rapid and efficient manner. Also, such a device must be relatively inexpensive to manufacture.

SUMMARY OF THE INVENTION

Therefore, the above and further objects of the present invention are realized by providing a new and improved body cavity tube securing device and a method of using it, wherein the tube can be immobilized quickly and efficiently, once the tube is inserted in place in a body cavity.

Another object of the present invention is to provide such a new and improved body cavity tube securing device and a method, wherein a body cavity tube is able to be securely immobilized in a manner which is relatively comfortable to the patient.

Briefly, the above and further objects of the present invention are realized by providing an improved securing device, which frictionally grips the body cavity tube in a secure manner. Also, the tube securing device of the present invention can be quickly attached to the tube and secured to the patient in a very efficient and effective manner.

Tube securing devices and method of using them are disclosed for immobilizing an endotracheal tube or the like in a body cavity such as in an intubated position. The device includes an elongated tube grasping arrangement having a ribbon securing device for helping to maintain the position of the tube grasping device in place. The tube grasping device includes a gripping portion disposed between its opposite ends to help limit sliding movement relative to the tube grasping assembly.

BRIEF DESCRIPTION OF THE DRAWINGS

The above mentioned and other objects and features of this invention and the manner of attaining them will become apparent, and the invention itself will be best understood by reference to the following description of the embodiment of the invention in conjunction with the accompanying drawings, wherein:

FIG. 3 is a pictorial view of another body cavity tube securing device, which is also constructed in accordance with the present invention;

FIG. 4 is a pictorial view of yet another body cavity tube securing device, which is constructed in accordance with the present invention;

FIG. 5 is a pictorial view of a further body cavity tube securing device, which is constructed in accordance with the present invention; and FIG. 6 is a pictorial view of yet a further body cavity tube securing device, which is constructed in accordance with the present invention.

BEST MODE FOR CARRYING OUT THE INVENTION

Figure 1:
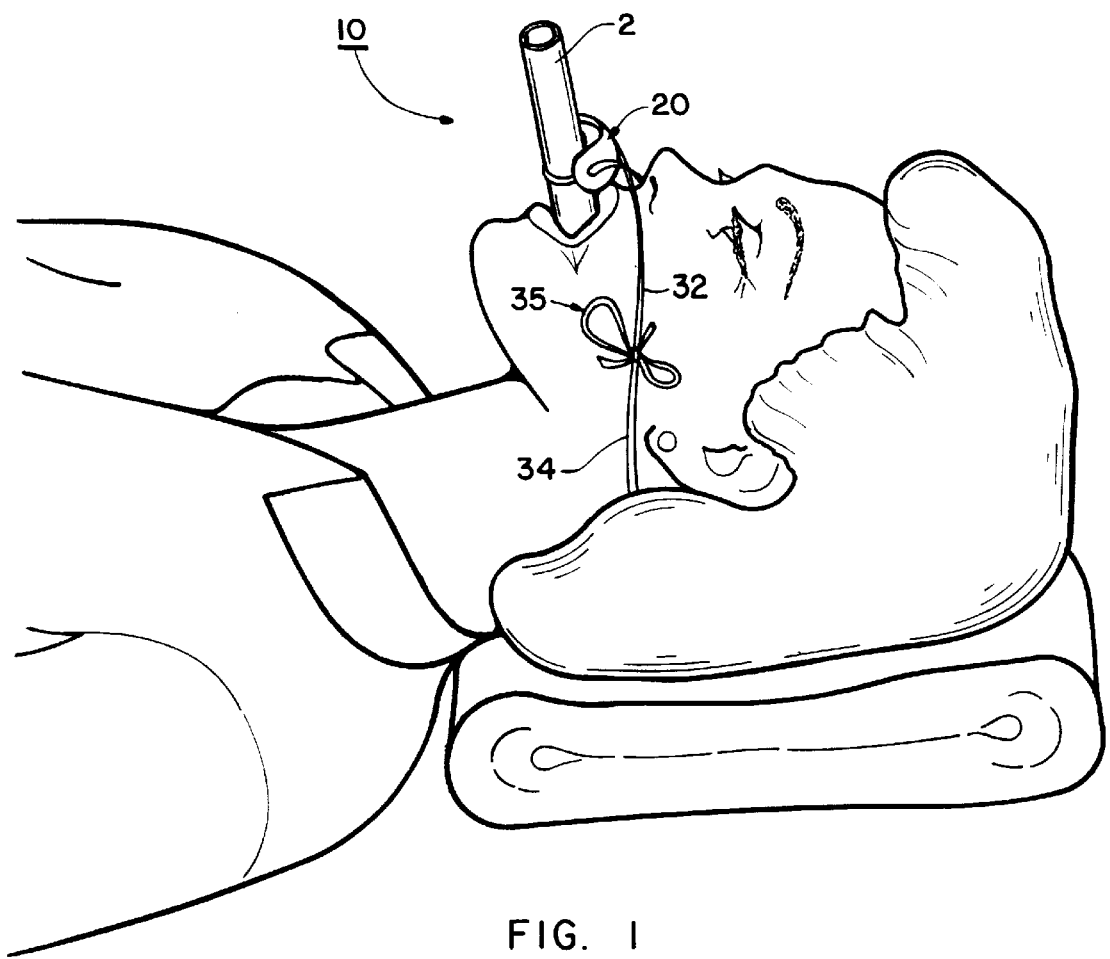
FIG. 1 is a pictorial view of a body cavity tube securing device, which is constructed in accordance with the present invention, and which is illustrated attached to a body cavity tube in the form of an endotrocheal tube inserted within the mouth of a patient.
Figure 2:
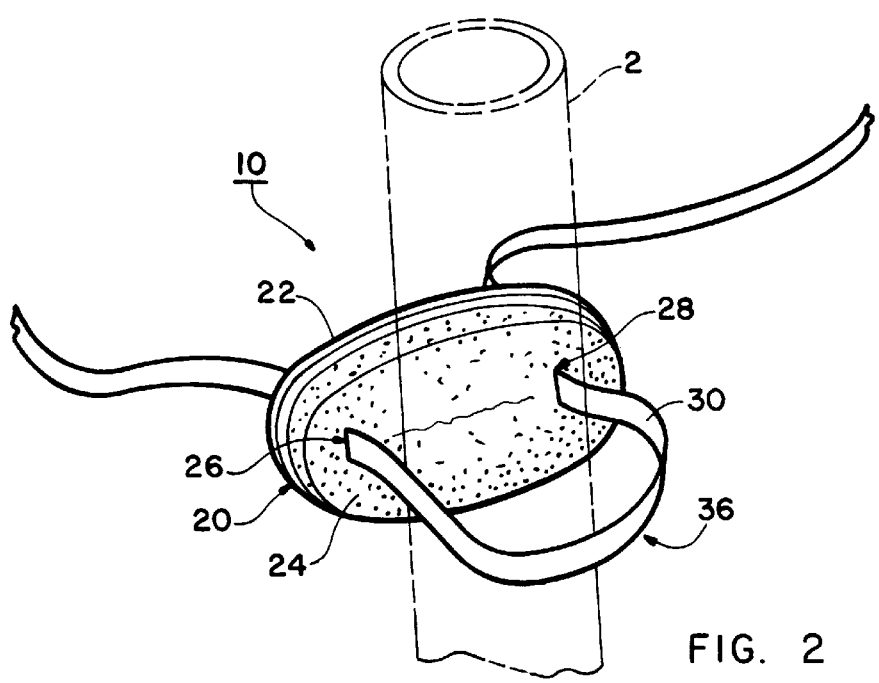
FIG. 2 is an enlarged pictorial view of the body cavity tube securing device of FIG. 1, illustrating it disposed apart from the body cavity tube.

Referring now to the drawings, and more particularly to FIGS. 1 and 2 thereof, there is shown a tube securing device 10, which is constructed in accordance with the present invention, and which is illustrated in a position to immobilize a body cavity tube 2 within a body cavity such as the mouth of a patient. As best seen in FIG. 2, the tube securing device 10 generally comprises a tube grasping assembly 20 which is firmly attached to the tube 2, which is usually composed of plastic material. The tube grasping assembly 20 includes a generally rectangular oval rigid backing member 22 having a gripping member 24 disposed thereon. The gripping member 24 is in the form of a foam pad which is pliable and engages frictionally the tube 2 which may be slippery when wet. Thus, the foam gripping member 24 can grip frictionally the smooth wet surface of the tube 22.

A pair of spaced-apart slits or openings 26 and 28 extend through opposite end portions of the gripping member 24 and receive a ribbon or other flexible line 30 therethrough, whereby the ribbon 30 can be wrapped about the head of the patient and a pair of distal end portions 32 and 34 can be tied in place in a knot 35 as indicated in FIG. 1. A bight 36 (FIG. 2) of the ribbon 30 in the form of a loop is adapted to surround the tube 2 and firmly press the tube 2 in engagement with the gripping member 24. In this regard, the bight 36 is disposed on the gripping member side of the backing member 22.

In use, the tube 2 is inserted within the mouth of the patient for intubation purposes, and the bight 36 of the ribbon 30 is slipped over the end of the tube 2, and the ribbon 30 is then tied about the head of the user by forming the knot 35. The ribbon is crossed in back of the tube grasping assembly 20 at 37 to provide a more secure gripping of the tube 2. However, it is to be understood that the ribbon need not be so crossed over onto itself as indicated in FIG. 1.

The backing member 22 is composed of suitable plastic material, and is pliable and flexible as indicated in FIG. 1 of the drawings. In this regard, the backing member 22 may be flexed about its mid point into a general C-shape to enable the gripping member 24 to assume a complementary C-shape to engage the outer surface of the tube 22 over a substantial surface area.

The foam gripping member 24 is composed of suitable thermoplastic foam material and is fixed to the backing member 22. The gripping member 24 also flexes with the flexible backing member 22 and provides a gripping member for firmly and frictionally grasping or engaging the outer surface of the tube 2. Thus, should the tube 2 become slippery as a result of being wetted with bodily fluids or from rain or other moisture from the surrounding environment, the foam gripping member 24 securely grips the tube 2.

Additionally, the foam gripping member 24 has a sufficient thickness throughout its length to cause, when flexed about its mid point, a sufficient area of engagement with the head of the patient to provide a comfortable means of attachment to the patient. In this regard, should the tube grasping assembly 20 come into engagement with the face of the user, such as at the mouth of the patient, the flexed foam gripping member 24 is the portion of the assembly 10 to engage the face of the person being intubated. A soft flexible foam gripping member 24 does not cause discomfort to the patient. It is to be understood that the tube grasping assembly 20 may not, in fact, need to engage the face of the user to secure the tube in place. The soft resilient foam gripping member 24 can secure the tube 20 without the necessity of engaging the patient.

Referring now to FIG. 3, there is shown a tube securing device generally indicated at 100, which is constructed in accordance with the present invention, and which is generally similar to the device 10 of FIG. 1, except that the manner of attaching the device 100 to a body cavity tube (not shown), such as the tube 2 of FIG. 1. The device 100 includes a tube grasping assembly 120, which is generally similar to the assembly 20 of FIG. 2. A pair of body engagable ribbons 130 and 132 are adapted to extend about the head of the patient and tied in place in a similar manner as the device 10 of FIG. 1. The ribbons 130 and 132 have distal ends (not shown) which are secured in place to the backside of the tube grasping assembly 120.

A pair of tube engagable ribbons 134 and 136 have respective distal end portions 137 and 139 fixed to the front face of the tube grasping assembly 120. A pair of opposite free distal ends 142 and 144 of the respective ribbons 134 and 136 are adapted to be affixed together to form a loop such as the loop or bight 36 of the device 10 of FIG. 2. In this regard, loop portion 138 of a Velcro material on one face of the ribbon 134 cooperates with a hook portion 140 of Velcro material on one face of the ribbon 136. In this manner, a pair of free ends 142 and 144 of the respective ribbons 134 and 136 can be moved as indicated by the curved arrow, into overlapping relationship with one another to enable the loop portion 138 to engage releasably the hook portion 140 to secure the tube grasping assembly 120 in engagement with a body cavity tube in a similar manner as shown in FIGS. 1 and 2 for the device 10. In order to quickly release the device 100, the distal end 142 can be readily separated from the end 144 so that a body cavity tube (not shown) similar to the tube 2 of FIG. 1 can be removed from the body cavity.

Referring now to FIG. 4, there is shown a tube securing device 200, which is also constructed in accordance with the present invention, and which is generally similar to the device 10 of FIG. 1, except that the device 200 includes a rigid backing member.

The tube securing device 200 generally comprises a tube grasping assembly 220, which is generally similar to the grasping assembly 20 of FIGS. 1 and 2. The assembly 220 includes a rigid backing member 222 which is generally rectangular in shape and is in the form of a relatively thick block preferably composed of thermal plastic material. A gripping member 224 in the form of a rectangular gently curved pad or block of foam material is fixed within a complimentary shaped curved recess 221 in the front face of the backing member 222 for gripping a body cavity tube (not shown) which may be similar to the tube 2 of FIG. 1. The gripping member 224, unlike the gripping member 24 of FIGS. 1 and 2, does not extend across the entire front face of the backing member 222, which is substantially longer than the length of the gripping member 224.

A pair of openings at 226 and 228 on the top edge or surface 229 of the backing member 222 receive a ribbon 230 which extends through a pair of passages 232 and 234 having the top edge openings 226 and 228 and a pair of side openings, such as the side opening 235 in the opposite side walls or surfaces, such as the side wall or surface 239. In this manner, ribbon end portions 231 and 233 extend from the opposite side wall openings, such as the side wall opening 235.

In use, the device 200 is attached to a body cavity tube (not shown) in a similar manner as the device 10 is attached to the tube 2 as shown in FIG. 1. However, due to the construction of the device 200, a bight 236 of the ribbon 230 secures a body cavity tube (not shown) to the foam gripping member 224 at an angular or cocked position relative to the tube, since the bight 236 of the ribbon 230 extends angularly downwardly from the top edge or surface 229 of the backing member 222 to grip the tube firmly into engagement with the member 224.

The passages 232 and 234 formed within the backing member 222 and extend in a smoothly curved manner between the opposite end openings, such as the openings 226 and 231.

Referring now to FIG. 5, there is shown a tube securing device 300, which is constructed in accordance with the present invention, and which is similar to the device 10 of FIGS. 1 and 2, except that the device 300 does not employ a foam gripping member. The device 300 generally comprises a tube grasping assembly 320, which employs a pair of generally C-shaped tube gripping members 322 and 324 which are hingedly connected together at 326 and releasably connected together at the opposite ends at 328 at a clasp mechanism. A pair of ribbons 330 and 332 are connected at opposite ends of the tube grasping assembly 320 in a similar manner as the device 100 of FIG. 3.

In use, the clasp 323 is released and the curved gripping members 322 and 324 are moved pivotally to an opened position by swinging them apart relative to the hinge 326. The grasping members 322 and 324 are then moved in surrounding engagement relative to a body cavity tube (not shown) and then pressed into clamping engagement with the tube. The clasp 328 is secured together to attach firmly the device 300 to the body cavity tube.

A pair of sets of teeth 323 and 325 are disposed on the inside curved surfaces of the respective grasping members 322 and 324, and are in the form of a large number of closely spaced flexible rods or pins to engage frictionally the body cavity tube. The teeth 323 and 325 are formed of thermoplastic material and are integrally connected to the inside curved surfaces of the respective gripping members 324 and 322. The teeth are conveniently cleanable due to their relative spacing to one another.

Referring now to FIG. 6, there is shown a tube securing device 400, which is constructed in accordance with the present invention, and which is similar to the device 10 of FIGS. 1 and 2, except that the device 400 does not employ a foam gripping member. The device 400 generally comprises a tube grasping assembly 420 having a flexible tube 421 composed preferably of thermoplastic material. A pair of spaced-apart oval shaped openings 422 and 424 near the opposite ends of the tube 421 receive a ribbon 430. In this regard, the ribbon 430 extends through a tube end 428 through the hollow interior of the tube 421 and out the oval opening 422 near the tube end 428. The ribbon 430 extends from the oval opening 422 through the other oval opening 424 to form a bight portion 432 therebetween. The ribbon 430 extends through the opening 424 into the hollow interior of the tube 421 and out the other tube and 429. In this manner, a tube (not shown), similar to the tube of FIG. 1, can be slipped between the bight portion 432 and the tube 421 as described in connection with the device 10. In this regard, the end portions 434 and 436 of the ribbon 430 extending from the opposite tube ends 428 and 429 can be wrapped about the head of the user as shown in FIG. 1, and then tied in place to cause the bight portion 432 to cinch the tube (not shown) securely in place within a body cavity.

A gripping member 426 is disposed along the outer surface of the tube 421 opposite the bight portion 432 of the ribbon 430 to enable the tube (not shown) similar to the tube 2 of FIG. 1, to be gripped in a friction tight manner. The gripping member 426 is in the form of a roughened or knurled surface of the tube 421.

While particular embodiments of the present invention have been disclosed, it is to be understood that various different modifications are possible and are contemplated within the true spirit and scope of the appended claims. There is no intention, therefore, of limitations to the exact abstract or disclosure herein presented.

What is claimed is:

1. A device for immobilizing a tube inserted within a body cavity, comprising:

an elongated tube grasping member having a pair of opposite ends;

an opposed securing member coupled to said tube grasping member at said opposite ends for surrounding a tube and for maintaining the position of such tube relative to said members, said securing member of sufficient length to extend substantially around the head of an individual and having distal ends releasably engagable, said securing member being adapted for extending partially about such tube and around a head of an individual for securing such tube to such head when fastened in place; and said tube grasping member for gripping a tube disposed between said opposite ends to help limit relative movement between said members and such tube; and means for connecting said members together pivotally.

2. A device according to claim 1, wherein said gripping means is disposed on both of said members disposed in confronting relationships.

3. A device according to claim 1, wherein said gripping means includes a plurality of teeth members.

* * * * *